(12) United States Patent
Robinson et al.

(10) Patent No.: US 6,706,091 B1
(45) Date of Patent: Mar. 16, 2004

(54) SUB- TO SUPER-AMBIENT TEMPERATURE PROGRAMMABLE MICROFABRICATED GAS CHROMATOGRAPHY COLUMN

(75) Inventors: Alex L. Robinson, Albuquerque, NM (US); Lawrence F. Anderson, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 29 days.

(21) Appl. No.: 10/326,033

(22) Filed: Dec. 17, 2002

(51) Int. Cl.[7] .............................................. B01D 15/08
(52) U.S. Cl. ................ 95/87; 95/89; 96/102; 96/105
(58) Field of Search ................ 73/23.35, 23.39, 73/23.41; 95/82, 87, 89; 96/101–107; 210/198.2

(56) References Cited

U.S. PATENT DOCUMENTS

| | | | | | |
|---|---|---|---|---|---|
| 3,149,941 | A | * | 9/1964 | Barnitz et al. ................. | 96/101 |
| 3,630,006 | A | * | 12/1971 | Sandoval ....................... | 96/101 |
| 4,350,586 | A | * | 9/1982 | Conlon et al. ............... | 210/149 |
| 4,534,941 | A | | 8/1985 | Stephens et al. .............. | 422/70 |
| 5,151,110 | A | * | 9/1992 | Bein et al. ..................... | 95/140 |
| 5,165,292 | A | * | 11/1992 | Prohaska ..................... | 73/866 |
| 5,250,093 | A | * | 10/1993 | Jiang et al. ................... | 96/102 |
| 5,376,252 | A | * | 12/1994 | Ekstrom et al. ............. | 204/603 |
| 5,544,276 | A | * | 8/1996 | Loux et al. .................. | 392/480 |
| 5,658,413 | A | * | 8/1997 | Kaltenbach et al. ..... | 156/272.8 |
| 5,720,798 | A | * | 2/1998 | Nickerson et al. ............. | 96/102 |
| 5,888,390 | A | * | 3/1999 | Craig ....................... | 210/198.2 |
| 5,935,430 | A | * | 8/1999 | Craig ....................... | 210/198.2 |
| RE36,350 | E | * | 10/1999 | Swedberg et al. ........ | 210/198.2 |
| 5,997,708 | A | * | 12/1999 | Craig ......................... | 204/601 |
| 6,068,684 | A | | 5/2000 | Overton et al. ............... | 96/104 |
| 6,171,378 | B1 | * | 1/2001 | Manginell et al. ............. | 96/143 |
| 6,258,263 | B1 | * | 7/2001 | Henderson et al. ...... | 210/198.2 |
| 6,296,685 | B1 | * | 10/2001 | Cammann et al. ............. | 95/45 |
| 6,454,840 | B1 | * | 9/2002 | Gellert et al. ................. | 96/101 |
| 6,459,080 | B1 | * | 10/2002 | Yin et al. .................... | 250/288 |
| 6,527,835 | B1 | * | 3/2003 | Manginell et al. ............ | 96/102 |
| 6,527,890 | B1 | * | 3/2003 | Briscoe et al. ........... | 156/89.11 |

OTHER PUBLICATIONS

Manginell et al., "Temperature Programmable Microfabricated Gas Chromatography Column", Patent Application No. 10/061,383, filed Jan. 31, 2002.
Mowry, et al., "Micropyrolyzer for Chemical Analysis of Liquid and Solid Samples", Patent Application No. 10/035,537, filed Oct. 23, 2001.
Frye–Mason et al., "Hand–Held Miniature Chemical Analysis System (PLUS CODE 83 IS NOT DEFINEDChem Lab) for Detection of Trace Concentrations of Gas Phase Analytes," Micro Total Analysis Systems 2000, 229 (2000).
Matzke, et al., "Microfabricated Silicon Gas Chromatographic MicroChannels: Fabrication and Performance," *Proceedings of SPIE, Micromachining and Microfabrication Process Technology IV*, 3511, 262 (1998).

* cited by examiner

Primary Examiner—Robert H. Spitzer
(74) Attorney, Agent, or Firm—Kevin W. Bieg (57) ABSTRACT

A sub- to super-ambient temperature programmable microfabricated gas chromatography column enables more efficient chemical separation of chemical analytes in a gas mixture by combining a thermoelectric cooler and temperature sensing on the microfabricated column. Sub-ambient temperature programming enables the efficient separation of volatile organic compounds and super-ambient temperature programming enables the elution of less volatile analytes within a reasonable time. The small heat capacity and thermal isolation of the microfabricated column improves the thermal time response and power consumption, both important factors for portable microanalytical systems.

14 Claims, 6 Drawing Sheets

SUB-TO SUPER-AMBIENT TEMPERATURE PROGRAMMABLE MICROFABRICATED GAS CHROMATOGRAPHY COLUMN

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention relates generally to chemical separations in microanalytical systems and, more particularly, to sub- to super-ambient temperature programming of a microfabricated gas chromatography column for efficient separation of high volatility analytes.

Portable, handheld microanalytical systems, which have been termed "chemical laboratories on a chip," are being developed to enable the rapid and sensitive detection of particular chemicals, including pollutants, high explosives, and chemical and biological warfare agents. These microanalytical systems should provide a high chemical selectivity to discriminate against potential background interferents and the ability to perform the chemical analysis on a short time scale. In addition, low electrical power consumption is needed for prolonged field use. See, e.g., Frye-Mason et al., "Hand-Held Miniature Chemical Analysis System ($\mu$ChemLab) for Detection of Trace Concentrations of Gas Phase Analytes," *Micro Total Analysis Systems 2000*, 229 (2000).

Current gas-phase microanalytical systems are based on gas chromatography (GC). Gas chromatography relies upon the chemical equilibria of analytes between a mobile phase and a stationary phase in a GC column to bring about a temporal separation of analytes in a gas mixture. Chemical equilibria and, therefore, column retention times are strongly influenced by column temperature. Thus, column temperature must be accurately controlled to obtain precise and reproducible separations.

The goal of a GC analysis is normally to obtain a separation with the required precision in the minimum time. Isothermal operation of the GC column can have drawbacks for achieving this goal with certain gas mixtures. If the selected isothermal temperature is too low, early eluted peaks may be adequately spaced but more strongly retained analytes will have broad and low-lying peaks with consequent poor detectability. This may also result in unacceptably long elution times. Conversely, the more strongly retained analytes will elute faster at a higher isothermal column temperature, but at the expense of poorer separation and loss of resolution for the early eluting analytes.

This general elution problem may be solved by temperature programming of the column. With temperature programming, analysis time can be reduced and the overall detectability of components can be improved. For example, for a given column it is possible to analyze gas mixtures with a broader volatility range in a shorter analysis time with temperature programming. For most analytes, the baseline resolution and peak widths are also improved. In general, temperature programming can comprise a series of changes in the column temperature that can include isothermal and controlled temperature rise segments. As an example of temperature programming, consider temperature ramping. Temperature ramping comprises monotonically increasing the temperature as the gas mixture is passed through the column. Higher volatility analytes in the mixture, which without temperature ramping pass through the column the earliest, still are the first to arrive at the column exit. Temperature ramping only tends to modestly improve the peak widths of these early eluting analytes and enhances baseline resolution somewhat. This is mainly due to the fact that these faster eluting analytes pass through the column before the initial temperature is appreciably increased. On the other hand, less volatile analytes, which in the absence of ramping tend to elute slowly with relatively broad and low-lying peaks, elute more quickly with temperature ramping and peak shapes are generally improved from the standpoint of baseline resolution and peak width. As a result, analysis time can be improved relative to a low temperature, isothermal elution while retaining peak resolution.

In conventional chromatography, an oven enclosing the GC column is used to effect the temperature program. This process is energy intensive, requiring hundreds of watts of power, and is capable of providing only modest ramp rates of about 25° C./min. These characteristics are adequate for laboratory applications where power is not that limited, and long, 30-meter columns can be used to separate difficult mixtures without the need for faster ramp rates. However, for portable applications, this level of power consumption is unacceptable. In addition, most conventional chromatographs only provide super-ambient temperature ramping. Given the necessarily shorter length of portable GC columns relative to laboratory instruments, sub-ambient and more rapid temperature ramping can compensate for the loss of resolution due to fewer theoretical plates in the portable GC column.

A temperature-controlled liquid chromatography column is disclosed in U.S. Pat. No. 4,534,941 to Stephens et al. That invention uses a plurality of thermoelectric modules to control the temperature of a long, tubular chromatographic column. The GC column is mounted on a notched side of a long thermal block and the plurality of thermoelectric modules are attached to the other, flat-surfaced side of the thermal block. Each thermoelectric module is attached to a separate heat sink that is actively cooled by airflow drawn through a plenum by a fan. Therefore, individual control of each of the plurality of thermoelectric modules is required to obtain adequate control of the column temperature. Because of the large thermal mass of this chromatography system, heating rates are limited to 12°–15° C. per minute. Further, the large system is not suitable to portable, handheld microanalytical systems.

A temperature programmable microfabricated gas chromatography ($\mu$GC) column has been disclosed in U.S. patent application Ser. No. 10/061,383, to Manginell and Frye-Mason, which is incorporated herein by reference. However, that $\mu$GC column was integrated with a resistive heating element, providing only super-ambient temperature ramping. Adequate separation of low-boiling-point, volatile compounds is difficult with such a super-ambient column.

The present invention solves the need for a sub- to super-ambient temperature programmable microfabricated GC column through the use of a thermoelectric cooler with temperature sensing on a microfabricated GC column. The present invention permits rapid, low-power and sensitive temperature programming of the microfabricated GC column with temperature ramping from sub-ambient temperatures that are an order of magnitude faster than conventional GC columns, thereby enabling more efficient separation of volatile compounds.

SUMMARY OF THE INVENTION

The present invention comprises a temperature programmable microfabricated gas chromatography column comprising a substrate, a channel etched in the substrate to separate chemical aralytes in a gas mixture, means for sealing the channel, and at least one thermoelectric cooler disposed on at least one surface of the substrate to heat the column from sub-ambient temperatures during the separation. The temperature programmable microfabricated gas chromatography column can further comprise a temperature sensor and a control board for electrical control of the thermoelectric cooler and fluidic control of, the column.

The present invention further comprises a method for separating a plurality of chemical analytes in a gas mixture, comprising cooling a temperature programmable microfabricated gas chromatography column to a sub-ambient temperature with a thermoelectric cooler, and injecting the gas mixture into the temperature programmable microfabricated gas chromatography column to separate the plurality of chemical analytes in the gas mixture. The method further comprises heating the column from a sub-ambient temperature to a higher temperature after injecting the gas mixture.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 4 shows chromatograms of mixtures of ten volatile organic compounds.

DETAILED DESCRIPTION OF THE INVENTION

The present invention comprises a sub- to super-ambient temperature programmable microfabricated GC column. The temperature control and ramping relies on a thermoelectric cooler (TEC) that is mounted between and in thermal communication with the $\mu$GC column and a heat sink. The TEC is bi-directional and can heat or cool the $\mu$GC column, depending on the polarity of the voltage applied to the TEC. Thermoelectric coupling, known as the Peltier effect, can provide a heat pump whereby heat is made to flow from a cold end to a warm end, depending upon the polarity of the applied voltage. The TEC comprises one or more junctions of two dissimilar conducting materials, one containing positive charge carriers (p-type) and the other negative charge carriers (n-type). When the p-n junction is reverse-biased (i.e., current flows from the n-type material to the p-type material), the dominant charge carriers move away from the junction and carry away heat, thereby cooling the junction. Heat flows in the opposite direction when the junction is forward biased.

The $\mu$GC column is preferably fabricated from a material having a high thermal conductivity, such as silicon, to provide rapid heat transfer to or from the TEC. A temperature gradient is achieved across the TEC by removal of excess heat or cold by the heat sink. A thermistor in thermal contact with the $\mu$GC can be used to monitor its temperature. The temperature ramp from sub- to super-ambient temperatures can be controlled with an electrical control circuit. By starting the temperature ramp at sub-ambient temperatures, the separation of quickly eluting analytes can be enhanced. By ramping the $\mu$GC to higher temperatures, more retained species can be forced to elute more quickly, thereby reducing overall analysis time. The technique can also be applied to liquid phase separations.

Figure 1:
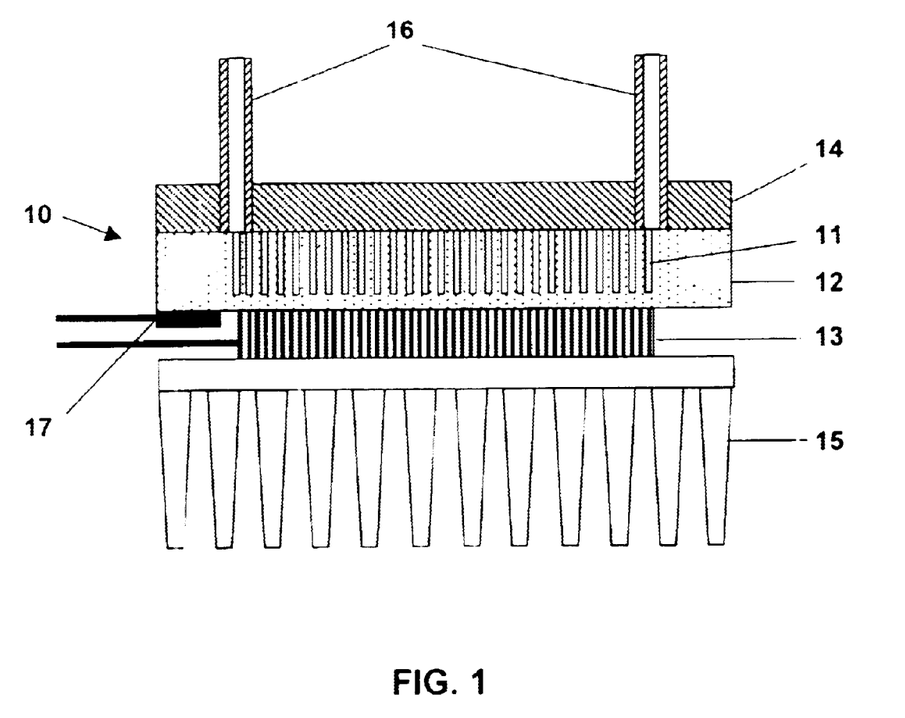
FIG. 1 shows a schematic side-view of a sub- to super-ambient temperature programmable microfabricated GC column.
Figure 2:
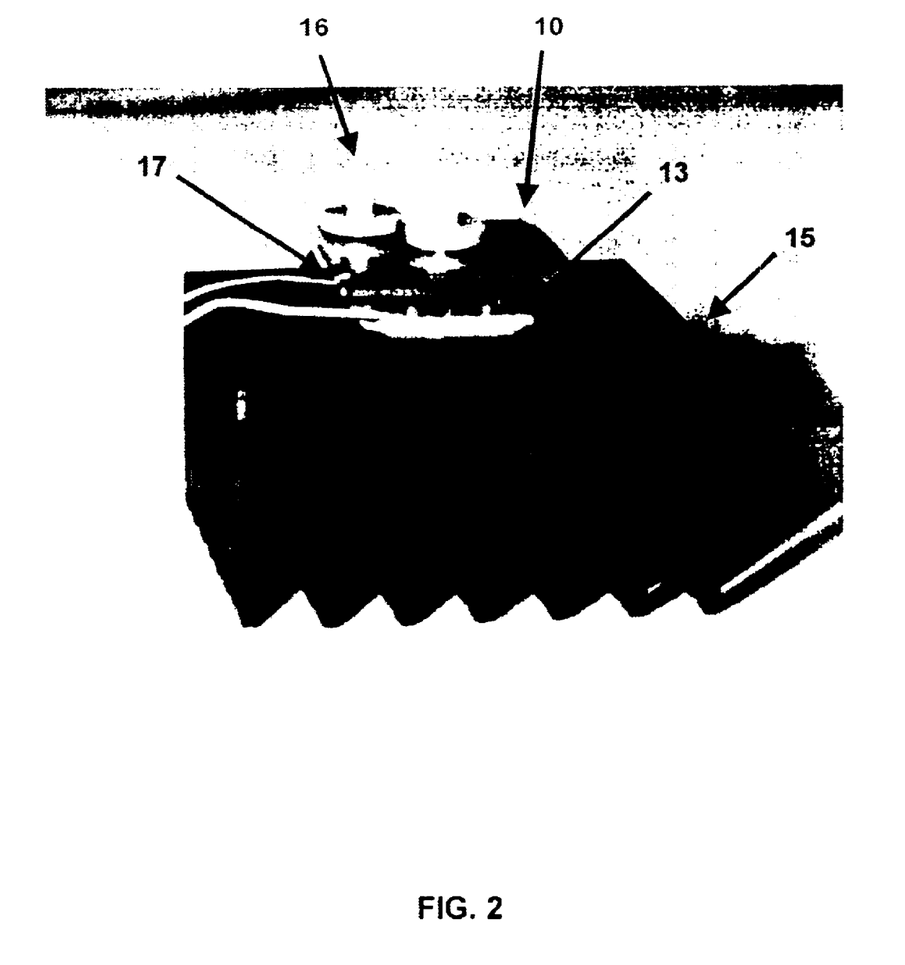
FIG. 2 shows a photograph of the sub- to super-ambient temperature programmable $\mu$GC column.

In FIG. 1 is shown a schematic illustration of the sub to super-temperature programmable $\mu$CG column 10 of the present invention, comprising a channel 11 formed in a substrate 12, a lid 14 to seal the channel 11, and a thermoelectric cooler 13 disposed on a surface of the substrate 12 to heat the column 10 during the separation of chemical analytes in a gas mixture. A heat sink 15 can be disposed on the other side of the thermoelectric cooler to provide for heat removal during cooling of the $\mu$GC column 10. The lid 14 or the substrate 12 can contain fluidic interconnects 16 to provide for fluid coupling to the channel 11. The $\mu$GC column 10 can further comprise a temperature sensor 17 for monitoring the temperature of the $\mu$GC column 10. An electrical controller (not shown) can be attached to the temperature sensor 17 and electrically connected to the thermoelectric cooler 13 to provide feedback control to the $\mu$GC column temperature. The resulting microfabricated GC column 10 provides advantages compared to conventional GC columns in terms of cost, system size, and power required to heat and temperature control the column. The configuration permits rapid temperature ramping of the $\mu$GC column 10 at a low power suitable for portable microanalytical applications.

Preferably, the temperature programmable microfabricated GC column 10 can be fabricated by etching the channel 11 in a side of the substrate 12 and bonding the lid 14 to the etched side of the substrate 12 to seal the channel 11. Alternatively, the channel 11 can be etched through the substrate 12 and lids 14 can be bonded to both sides of the substrate 12 to seal the channel 11. Alternatively, two substrates 12 with mirror image channels 11 can be bonded to form a single column. The substrate 12 can comprise a substantially planar sheet or plate of silicon, glass, ceramic, or other suitable GC column material. For example, the substrate 12 can be a single crystal silicon wafer. Inlet and outlet tubes 16 can be attached through the lid 14 or directly through the substrate 12 to the channel 11 in the substrate 12.

The channel 11 for the $\mu$GC column 10 can be formed in the substrate 12 by a variety of processes such as those described by Matzke et al., "Microfabricated Silicon Gas Chromatographic MicroChannels: Fabrication and Performance," *Proceedings of SPIE, Micromachining and Microfabrication Process Technology* IV, 3511, 262 (1998) and in U.S. Pat. No. 6,068,684 to Overton, which are incorporated herein by reference. For example, the channel 11 can be a deep high-aspect-ratio channel formed in the side of the substrate 12 by anisotropic wet etching or plasma etching. The high-aspect-ratio cross-section enables close packing of a spiral or serpentine channel 11 to achieve a desired column length. A typical microfabricated silicon-based GC column 10 comprises a 1-meter spiral channel 11 formed on a 1.2 cm² area of a silicon wafer 12. A typical channel 11 has a cross-section that is 100 µm wide by 400 µm deep. The inside surfaces of the channel 11 can be coated with a stationary phase material to enhance the separation of the chemical analytes of interest in the gas mixture to be analyzed. The stationary phase material can be a polymer having a specific chemical group with the proper physico-chemical interaction to cause separation of the analytes. The channel 11 can be coated with the stationary phase material by a number of methods. Severally commonly used methods include pushing a plug of the material through the channel 11, filling the channel 11 with a solvent containing the stationary phase material and then applying a vacuum to the end of the channel 11 to dry the solvent out of the channel 11, or by using sol-gel techniques. Instead of using a stationary phase material to coat the surfaces of the channel 11, the channel can alternatively be filled with a porous packing material to make a microfabricated packed GC column.

The lid 14 is preferably a thermally insulating material and thin to minimize the heat capacity of the column 10. The lid 14 can be made from a thin sheet of a material such as glass or polymer. For example, the lid 14 can be a machined Pyrex lid that is anodically bonded to the deep-etched silicon wafer 12. The Pyrex lid 14 can be less than 1 mm in thickness, and preferably about 250 µm or less in thickness. Inlet and outlet holes can be formed in the lid 14, for example, by grinding or ultrasonic drilling. Following bonding of the lid 14 to the substrate 12, the channel 11 can be cleaned, for example, with a sulfuric acid/hydrogen peroxide clean. Tubes 16 can be capillary tubes that are attached, for example with epoxy, to the inlet and outlet holes in the lid 14 to fluidically connect the channel 11 to the control board.

The thermoelectric cooler 13 can be a commercially available Peltier cooler. A number of manufacturers provide such thermoelectric coolers, such as Melcor or Marlow industries. The thermoelectric cooler 13 is preferably capable of producing at least a 25° C. temperature gradient, and should be large enough to cover the channel 11. The heat sink 15 is preferably at least as large as the thermoelectric cooler 13 to keep the side distal to the µGC near ambient temperature. A fan (not shown) appropriately sized for the heat sink 15 can aid in heat transfer. However, a heat sink 15 with sufficiently larger dimensions than the thermoelectric cooler 13 can obviate the need for the fan. For example with the µGC described above, a 0.375×0.375 inch thermoelectric cooler 13 with a 1.0×1.0×0.75 inch (W×L×H) aluminum heat sink 15 with no fan will allow thermostasis and ramping between −6 and +83° C.

Various types of temperature sensors 17 can be used to sense the column temperature in a feedback loop, including diodes, thin film thermistors, thermocouples, and thermopiles. The electrical control circuit (not shown) should supply a voltage to the thermoelectric cooler 13 to affect a constant or changing temperature, with the output voltage depending upon the return signal from the temperature sensor 17. The output voltage may be of various types, such as continuously variable (Class A, B) or pulsed (Class D). The electrical controller should also be able to automatically change the polarity of the voltage to the thermoelectric cooler 13 to provide temperature increases and decreases. The control time constant may require modification to dampen or prevent oscillations between the actual temperature and the feedback temperature sensor.

In a typical GC analysis, the µGC is cooled to the desired temperature. A plug of the gas mixture to be analyzed is then injected into the channel 11 via the inlet tube 16. For example, a gaseous plug can be generated by the rapid release of sorbed chemical species from a chemical preconcentrator, as disclosed in U.S. Pat. No. 6,171,378 to Manginell et al., or by the rapid vaporization of a liquid sample or pyrolyzation of a solid sample by a micropyrolyzer, as disclosed in U.S. patent application Ser. No. 10/035,537 to Mowry, et al., both of which are incorporated herein by reference. The column 10 is then heated by the thermoelectric cooler 13 according to a prescribed temperature program. The analytes in the injected gas mixture are thereby separated with their retention time being dependent on the physico-chemical properties of the channel 11 and the temperature program. The separated analytes then exit the channel 11 through the outlet tube 16 and pass over a detector that measures some property of the gas, such as thermal conductivity, partitioning into a mass sensor coating, or ionizability during combustion. A chromatogram, showing detector response versus retention time, can thereby be recorded.

Chromatograms of mixtures of volatile organic compounds were obtained with a temperature programmable microfabricated GC column 10, comprising an 98 cm long× 75 µm wide×400 µm deep channel 11 etched in a 1.3 cm×1.3 cm×525 µm thick silicon wafer 12. The channel 11 was coated with a stationary phase comprising PDMS. A thermoelectric cooler 13, having dimensions of 0.375×0.375 inch, was mounted on the substrate side of the µGC 10 opposite the channel 11. The channel 11 was sealed by a 500 µm thick Pyrex lid 14 on the channel side of the substrate 12. The column temperature was monitored by a thermistor temperature sensor 17 mounted adjacent to the thermoelectric cooler 13 on the silicon wafer 12 and connected to an electronic control circuit. A 1.5×1.5×0.5 inch heat sink 15 was attached to the thermoelectric cooler 13 using thermally conductive epoxy. No fan was required to increase airflow over the heat sink. The channel 11 was fluidically connected to the injection port and the flame ionization detector (FID) of a commercially available gas chromatographic instrument. A pressure of 5.0 p.s.i.g. provided flow rates of 0.9–1.8 mL/min of nitrogen, depending upon the instantaneous temperature of the channel 11.

Because the thermoelectric cooler 13 is in good thermal contact with the low heat capacity column 10, heating rates of 0.65° C./sec require an average of 420 mW of power. Using a directly connected power supply, heating rates over 20° C./sec can be achieved with less than 11 W of power. Using maximum power from the electrical controller circuit (2.5 W), ramp rates up to 10° C./sec are possible. A typical Melcor thermoelectric cooler can be rated up to 67° C. for the hot side when the cold side is held at 25° C. These temperatures can be safely exceeded for short periods of time. By staging two or more thermoelectric coolers, the hot side temperature can berated up to 131° C., for a 106° C. temperature differential. By holding the hot side at 25° C. the cold side of the thermoelectric cooler can approach the same temperature differentials, however undesirable effects such as condensation and frosting can occur. Using the electrical controller circuit and the single thermoelectric cooler, only 400 mW is required to hold the µGC at 86° C. For a small thermoelectric cooler the maximum current rating is generally 800 mA, greater than the current allowed by our controller circuit (500 mA). Thus, greater ramp rates could be expected under optimal conditions. Also, higher currents are required for larger thermoelectric coolers. Melcor and other vendors make controllers rated to deliver 10 amps of current or more for these needs. The heating and cooling rates for the µGC system described above are about an order of magnitude faster than conventional GC ovens and consume at least two orders of magnitude less power.

Figure 3:
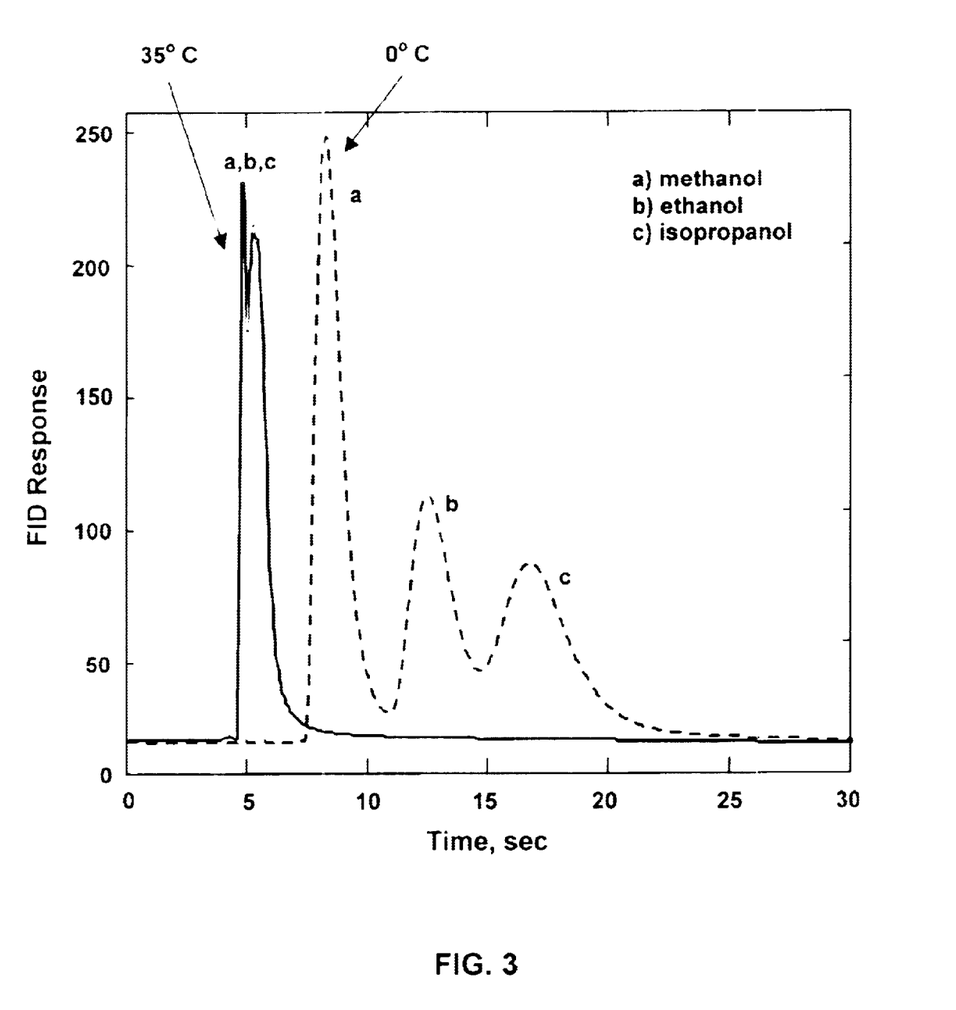
FIG. 3 shows chromatograms of a mixture of lower alcohols obtained at $\mu$GC column temperatures of 0° C. and 35° C.

In FIG. 3 are shown chromatograms of a mixture of lower alcohols obtained at isothermal column temperatures 0° C. and 35° C. A FID was used to detect the analytes. All three alcohols elute very quickly from the column at 35° C. at an analyte flow rate of 1.0 mL/min, resulting in inadequate separation of the Its alcohols. Good separation of the alcohols is achieved when the same column is cooled to 0° C. with the thermoelectric cooler. Despite the higher flow rate of 1.6 mL/min, the alcohols are more strongly retained in the channel of the μGC at the lower temperature.

Figure 4A:
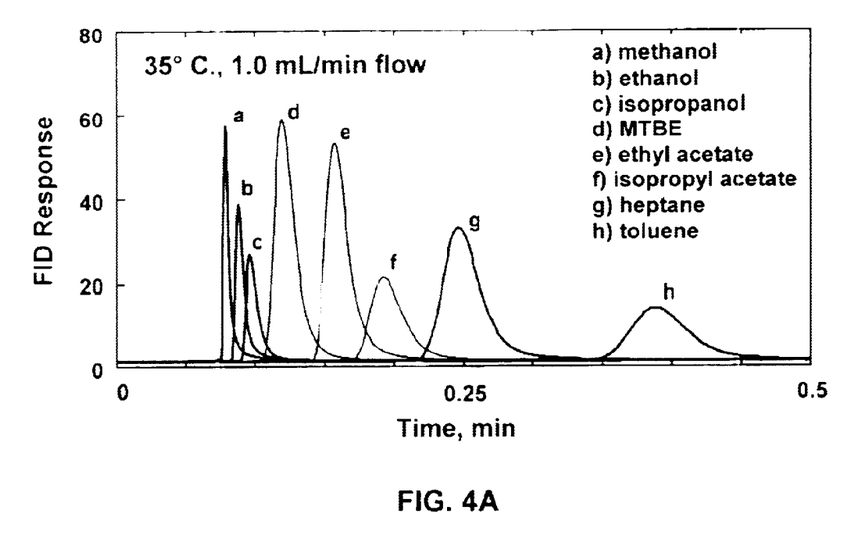
FIG. 4A shows chromatograms obtained at a $\mu$GC column temperature of 35° C.
Figure 4B:
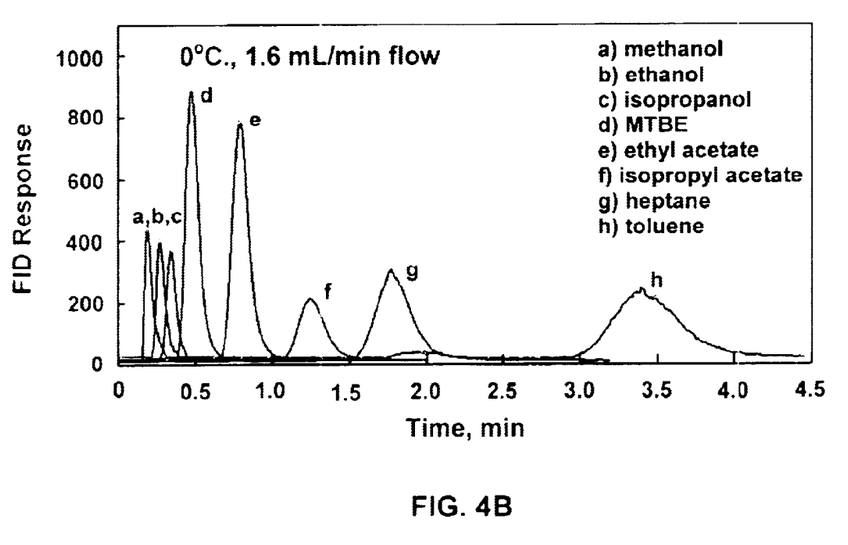
FIG. 4B shows chromatograms obtained at a $\mu$GC column temperature of 0° C.

In FIG. 4 are shown composite chromatograms of eight chemical analytes having a wide volatility range, obtained at isothermal column temperatures of 35° C. (FIG. 4A) and 0° C. (FIG. 4B). The analyte set consisted of low-boiling-point organic compounds, including methanol, ethanol, isopropyl alcohol, methyl tert-butyl ether (MTBE), ethyl acetate, and as well as less volatile organics, including isopropyl acetate, heptane, and toluene. In FIG. 4A is shown a composite chromatogram of the analyte set obtained at a column temperature of 35° C. The high column temperature provided a fast elution, but inadequate separation of the volatile, early eluting analytes. In FIG. 4B is shown a composite chromatogram of the analyte set obtained at a column temperature of 0° C. The low column temperature provided better resolution of the more volatile organic compounds, but the stronger retained analytes, such as toluene, did not elute within a reasonable amount of time.

Figure 5:
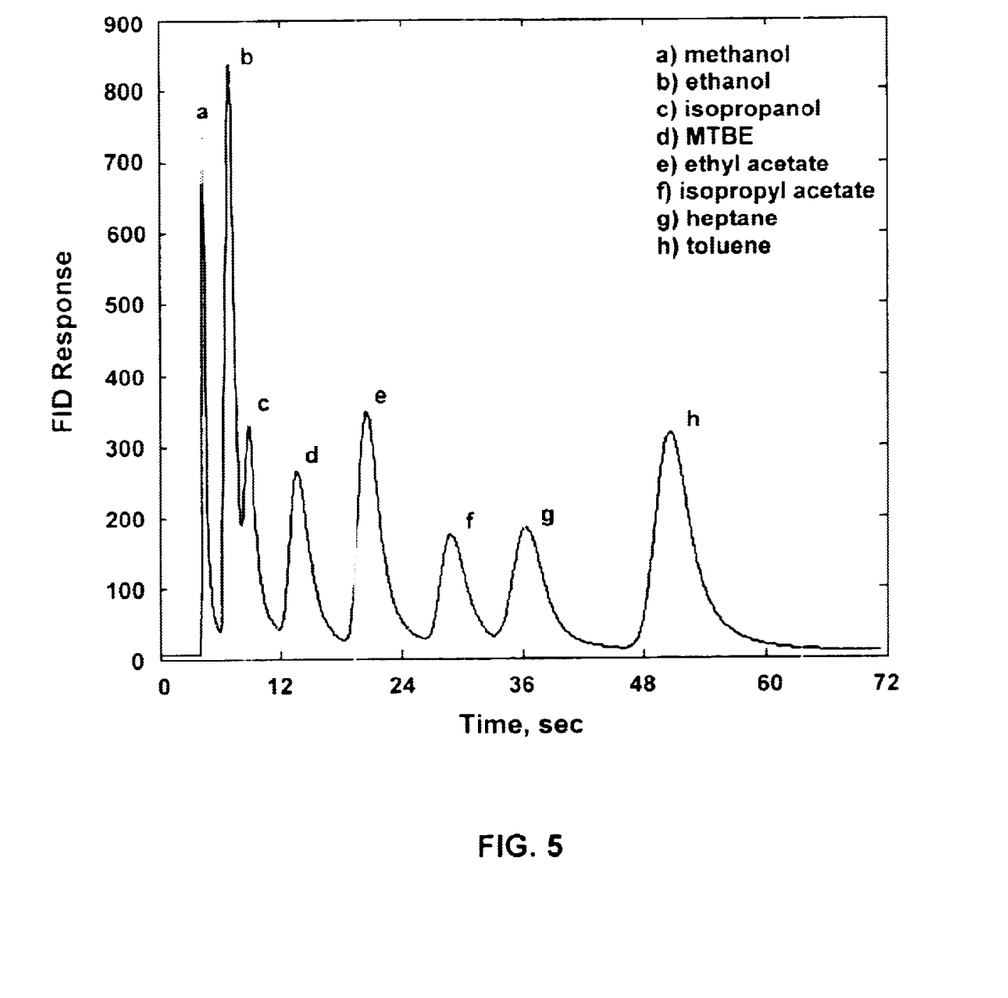
FIG. 5 shows a chromatogram of all ten compounds obtained with a temperature program of the $\mu$GC column comprising a sub-ambient isothermal segment followed by a ramp to a super-ambient temperature.

Good separation of all of the analytes in the analyte set can be obtained within a reasonable time with suitable sub- to super-ambient temperature programming of the μGC column. The temperature programming can include a sub-ambient isothermal segment, to provide good separation of the more volatile analytes, and a controlled temperature rise segment, to provide for elution of the less volatile analytes within a reasonable time. The chromatogram in FIG. 5 shows the separation of a mixture of all eight analytes achieved with a temperature program providing a 5 sec. segment at a column temperature of 5° C. followed by a 55 second temperature ramp to 60° C. (i.e., a heating rate of 60° C./min). All eight analytes are nearly resolved with this temperature program. The initial low temperature segment provides good separation of the higher volatility analytes and the temperature ramp segment provides good detectability of the lower volatility analytes.

Figure 6:
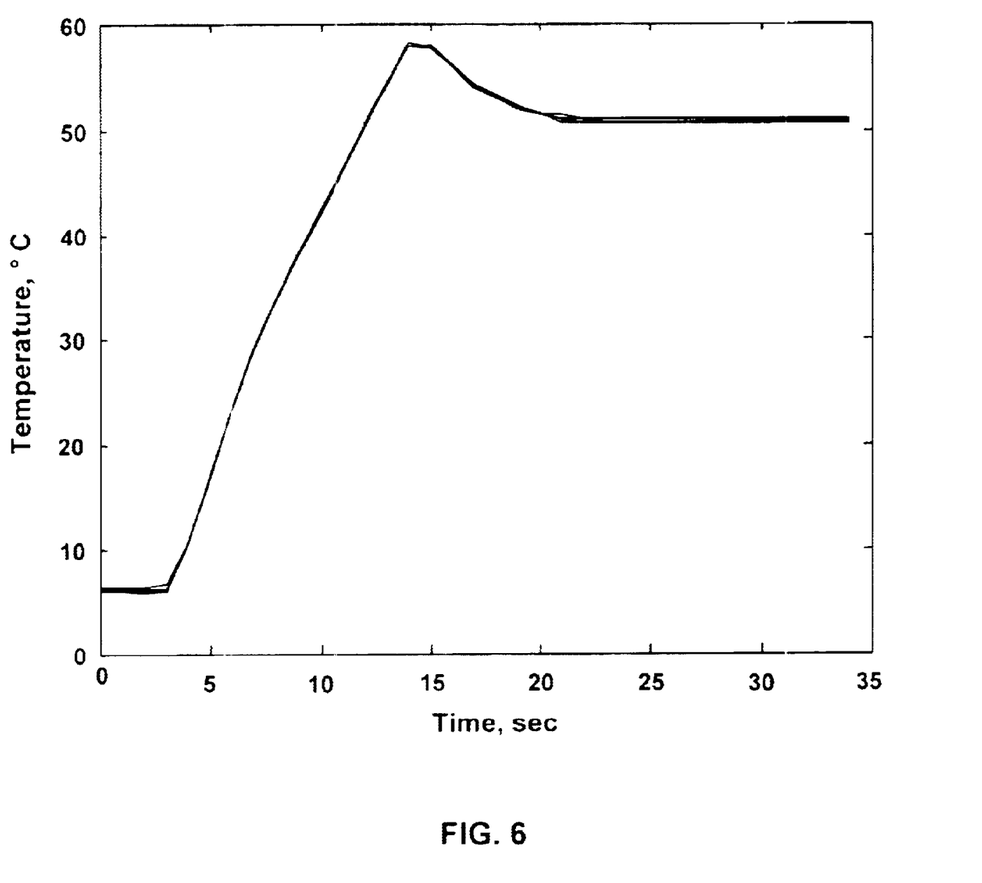
FIG. 6 shows the $\mu$GC column temperature for four sequential temperature ramps.

FIG. 6 shows the μGC temperature for four sequential temperature ramps. The program called for a linear ramp from 6 to 51° C. in 10 seconds. The slightly concave curvature resulted from the non-linear response of the thermistor. Indeed, ramping with the maximum current (500 mA) allowed by the controller circuit showed instantaneous ramp rates exceeding 5° C./sec over this range. Correcting for this thermistor effect straightens out the curve. The average point-by-point standard deviation across the four runs was less than 0.2° C. Doubling the ramp time to 20 seconds decreased the point-by-point standard deviation to 0.1° C. Forced cooling lowered the temperature more slowly, with an average rate of 3° C./sec to return to the initial temperature. The temperature difference between the center and the outer edge of the μGC was less than 0.8° C. during the ramps, and 0.5° C. cooler at equilibrium at the upper temperature. This can be attributed to the thermoelectric cooler being smaller than the footprint of the silicon substrate containing the channel. A larger thermoelectric cooler should eliminate this effect.

These data show that temperature programming of a microfabricated GC column 10 with a thermoelectric cooler 13 can significantly improve separation of some gas mixtures comprising volatile organic compounds. Furthermore, temperature programming partially compensates for the limited number of plates available in short microfabricated columns, as compared with longer conventional laboratory GC columns. This microfabricated GC column with thermoelectric temperature control provides an important component for energy efficient, portable microanalytical systems for the detection of volatile compounds.

The embodiments of the present invention have been described as a temperature programmable microfabricated gas chromatography column capable of sub- to super-ambient temperature ramping. It Will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for separating a plurality of chemical analytes in a gas mixture, comprising:
providing a temperature programmable microfabricated gas chromatography column, comprising:
a substrate having a first surface and a second surface;
a sealed channel formed in at least one of the first surface and the second surface of the substrate; and
at least one thermoelectric cooler disposed on at least one of the first surface and the second surface of the substrate;
cooling temperature programmable microfabricated gas chromatography column to a sub-ambient temperature with a the at least one thermoelectric cooler, and
injecting the gas mixture into the channel to separate the plurality of chemical analytes in the gas mixture.

2. The method of claim 1, further comprising heating the column from the sub-ambient temperature to a higher temperature after injecting the gas mixture.

3. The method of claim 2, wherein the column is heated to a super-ambient temperature.

4. The method of claim 2, wherein the heating comprises a temperature ramp.

5. The method of claim 4, wherein the temperature ramp is greater than 0.1° C./sec.

6. The method of claim 4, wherein the temperature ramp is greater than 1° C./sec.

7. The method of claim 4, wherein the temperature ramp is greater than 10° C./sec.

8. The method of claim 1, wherein the step of injecting the gas mixture comprises releasing the plurality of chemical analytes from a sorptive material.

9. The method of claim 8, wherein the releasing the plurality of chemical analytes comprises heating the sorptive material in a chemical preconcentrator.

10. The method of claim 1, wherein the step of injecting the gas mixture comprises vaporizing the plurality of chemical analytes from a liquid sample.

11. The method of claim 10, wherein the vaporizing the plurality of chemical analytes comprises heating the liquid sample in a micropyrolyzer.

12. The method of claim 1, wherein the step of injecting the gas mixture comprises pyrolyzing the plurality of chemical analytes from a solid sample.

13. The method of claim 12, wherein the pyrolyzing the plurality of chemical analytes comprises heating the solid sample in a micropyrolyzer.

14. The method of claim 1, wherein the step of injecting the gas mixture comprises releasing the plurality of chemical analytes from a sample injection loop.

* * * * *